US009034845B2

(12) United States Patent
Mailland et al.

(10) Patent No.: US 9,034,845 B2
(45) Date of Patent: May 19, 2015

(54) COMPOSITIONS FOR TREATING ROSACEA

(75) Inventors: Federico Mailland, Lugano (CH);
Emanuela Mura, Como (IT)

(73) Assignee: POLICHEM SA, Luxembourg (LU)

(*) Notice: Subject to any disclaimer, the term of this patent is extended or adjusted under 35 U.S.C. 154(b) by 157 days.

(21) Appl. No.: 12/931,486

(22) Filed: Feb. 2, 2011

(65) Prior Publication Data

US 2011/0207696 A1 Aug. 25, 2011

Related U.S. Application Data

(63) Continuation-in-part of application No. PCT/EP2009/059749, filed on Jul. 28, 2009.

(30) Foreign Application Priority Data

Aug. 5, 2008 (EP) ..................... 08161799

(51) Int. Cl.
A61K 31/722 (2006.01)
A61K 31/16 (2006.01)
A61P 17/00 (2006.01)
A61K 45/06 (2006.01)
A61K 8/362 (2006.01)
A61K 8/37 (2006.01)
A61K 8/42 (2006.01)
A61K 8/73 (2006.01)
A61K 9/00 (2006.01)
A61K 31/194 (2006.01)
A61K 31/20 (2006.01)
A61K 31/23 (2006.01)
A61Q 19/00 (2006.01)
A61K 47/10 (2006.01)
A61K 47/14 (2006.01)
A61K 47/18 (2006.01)
A61K 47/24 (2006.01)
A61K 47/36 (2006.01)
A61K 47/42 (2006.01)

(52) U.S. Cl.
CPC .................. *A61K 45/06* (2013.01); *A61K 31/16* (2013.01); *A61K 8/362* (2013.01); *A61K 8/37* (2013.01); *A61K 8/42* (2013.01); *A61K 8/736* (2013.01); *A61K 9/0014* (2013.01); *A61K 31/194* (2013.01); *A61K 31/20* (2013.01); *A61K 31/23* (2013.01); *A61K 31/722* (2013.01); *A61K 47/10* (2013.01); *A61K 47/14* (2013.01); *A61K 47/183* (2013.01); *A61K 47/24* (2013.01); *A61K 47/36* (2013.01); *A61K 47/42* (2013.01); *A61Q 19/00* (2013.01)

(58) Field of Classification Search
None
See application file for complete search history.

(56) References Cited

U.S. PATENT DOCUMENTS

| 4,780,310 | A | 10/1988 | Lang et al. |
| 6,451,773 | B1 * | 9/2002 | Oester et al. ..................... 514/55 |
| 6,734,210 | B2 * | 5/2004 | Hebert ........................... 514/460 |
| 2004/0081672 | A1 | 4/2004 | Gupta |
| 2004/0156873 | A1 | 8/2004 | Gupta |
| 2006/0024339 | A1 * | 2/2006 | Murad .......................... 424/401 |
| 2008/0069779 | A1 | 3/2008 | Tamarkin |
| 2010/0062083 | A1 * | 3/2010 | Mailland et al. .............. 424/725 |

FOREIGN PATENT DOCUMENTS

| EP | 1978056 | 10/2008 | |
| JP | 05-339152 | * 12/1993 | ............... A61K 9/70 |
| JP | 2001-512471 | 8/2001 | |
| JP | 2004504333 | 2/2004 | |
| JP | 2005518399 | 6/2005 | |
| JP | 2006-306899 | 11/2006 | |
| JP | 2007-513907 | 5/2007 | |
| WO | WO 0174165 | 10/2001 | |
| WO | WW 0174165 | 10/2001 | |
| WO | WO 2004068970 | 8/2004 | |
| WO | WW 2004068970 | 8/2004 | |
| WO | WO 2004082628 | 9/2004 | |
| WO | WW 2004082628 | 9/2004 | |
| WO | WO 2006010590 | 2/2006 | |
| WO | WW 2006010590 | 2/2006 | |
| WO | WO 2007084998 | 7/2007 | |
| WO | WW 2007849998 | 7/2007 | |
| WO | WO 2007086211 | 8/2007 | |
| WO | WW 2007086211 | 8/2007 | |
| WO | WO 2007149868 | 12/2007 | |
| WO | WW 2007149868 | 12/2007 | |
| WO | WO 2008038147 | 4/2008 | |
| WO | WW 2008038147 | 4/2008 | |
| WO | WO 2008/098634 | * 8/2008 | ............... A61K 8/73 |

OTHER PUBLICATIONS

Harada et al., machine translation of JP 05-339152, original document published Dec. 1993.*
International Preliminary Report on Patentability for PCT/EP2009/059749 of Aug. 6, 2010.
International Search Report for PCT/EP2009/059749 of Nov. 25, 2009.
Maramaldi G., et al., "Potassium Azeloyl Diglycinate: A Multifunctional Skin Lightener" Cosmetics and Toiletries, vol. 117, No. 3, Mar. 1, 2002, p. 43,44,46,48, 50.
Rigano, L., et al., "Problem Skin Physiological and Hygienic Treatments" Cosmetic Technology, vol. 8, No. 5, p. 17-25, 2005.
Monti, D., et al., 2005, Drug Dev Ind Pharm, 31(1):11-7 Abstract.
Fitzpatrick's Dermatology in General Medicine, 6th Edition, vol. 1, Ed. Freedburg, et al., McGraw-Hill, USA, 2003.
Guglielmini, Azelaic acid derivative clearly improves skin; Personal Care Magazine, Jan. 2008; http://www.personalcaremagazine.com/print.aspx?Story=3278.

* cited by examiner

Primary Examiner — Shaojia Anna Jiang
Assistant Examiner — Bahar Craigo
(74) Attorney, Agent, or Firm — Hueschen and Sage

(57) ABSTRACT

The present invention is directed to compositions containing chitosan, a chitosan derivative or a physiologically acceptable salt thereof, and a short-medium chain dicarboxylic acid amide, or a physiologically acceptable salt thereof, forming a film after application onto the skin, useful for protecting skin of the face and of other affected areas in couperose, rosacea and telangiectasia of the legs.

15 Claims, 1 Drawing Sheet

Percentages of subjects by flushing severity at baseline and at end of treatment (28 days) with the preparation as per Example 8 (P-3075) or placebo.
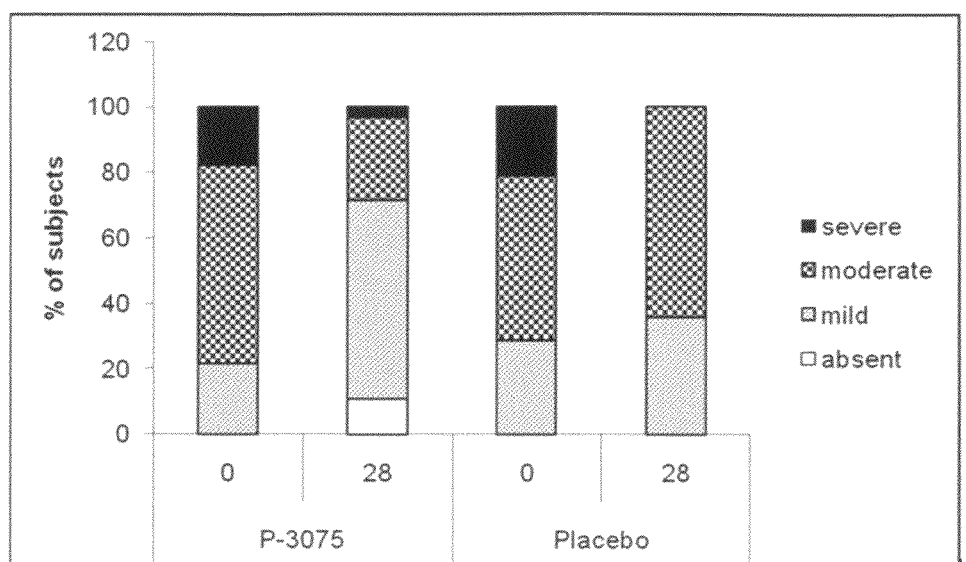

COMPOSITIONS FOR TREATING ROSACEA

BACKGROUND OF THE INVENTION

The present invention relates to compositions containing chitosan, a chitosan derivative or a physiologically acceptable salt thereof, and a short-medium chain dicarboxylic acid amide, or a physiologically acceptable salt thereof, for the preparation of a medicament, or a medical device, or a sanitary product, or a cosmetic, forming a film after application onto the skin of the face and of other affected areas, useful for protecting skin in rosacea, a chronic inflammatory condition of the skin, and other skin conditions characterized by telangiectasia, like couperose and leg telangiectasia.

FIELD OF THE INVENTION

Rosacea is a common but often misunderstood condition that is estimated to affect over 13 million people worldwide (Plewig & Jansen in: Fitzpatrick's Dermatology in General Medicine. Freedberg et al. Eds., 6$^{th}$ ed., McGRAW-HILL pub., NY 2003, p. 688). It affects white-skinned people of Celtic or northern European descent, and has been named the 'curse of the Celts'. It is rarer in dark-skinned people, like American and African blacks.

It begins as erythema (flushing and redness, also called "couperose") on the central face and across the cheeks, nose, or forehead but can also less commonly affect the neck and chest. As rosacea progresses, other symptoms can develop such as semi-permanent erythema, telangiectasia (dilation of superficial blood vessels on the face), red domed papules (small bumps) and pustules, red gritty eyes, burning and stinging sensations, and in some advanced cases, a red lobulated nose (rhinophyma). The disorder can be confused with, and co-exist with acne vulgaris and/or seborrhoeic dermatitis. Rosacea affects both sexes, but is almost three times more common in women, is common in the third and fourth decade and peaks between the ages of 40 and 50 years. The presence of rash on the scalp or ears suggests a different or co-existing diagnosis, as rosacea is primarily a facial diagnosis.

The pathogenesis of rosacea in unknown, and various factors have been suspected to contribute to this condition. Among the various factors, the following have been claimed to play a role: degenerative changes of the perivascular/vascular collagen, that lead to small vessel dilatation resulting in flushing, telangiectasia, erythema; perivascular leakage of potentially inflammatory substances; abnormal tissue response to cytokines and other mediators; use of topical drugs (corticosteroids). Exposure to temperature extremes can cause the face to become flushed as well as strenuous exercise, heat from sunlight, severe sunburn, cold wind, moving from cold to hot environment. There are also some foods and drinks that can trigger flushing, these include alcohol, caffeine (hot tea and coffee), and spicy food. Microorganisms also have been claimed to contribute to the development or complicate rosacea, like *Demodex folliculorum*, *Helicobacter pylori* or *Propionibacterium acnes*.

Treatment of rosacea is inconclusive. Systemic or topical treatments include antibiotics, metronidazole and antifungals; retinoids, some beta blockers, spironolactone. No causal treatment has ever been proposed, and lifelong symptomatic treatment is often necessary, as just few cases may go into a permanent remission of the symptoms. Long term treatment of rosacea is limited by the intrinsic toxicity of drugs.

Leg telangiectasia consists in very thin varicose capillaries, with a caliber within 0.1 and 1 mm, that are classified as follows:

1) Telangiectasia due to venous insufficiency, accompanied by other clinical signs of venous insufficiency. They are localized at the foot back, retromalleolar region, legs, and at the medial thigh surface.
2) Telangiectasia due to hormonal abnormalities, localized at the medial and anterolateral thigh surface. They spontaneously occur during menarche, menopause, pregnancy or under contraceptive treatment.
3) Very thin telangiectasia due to constitutional weakness of the capillary system, mainly at the distal portion of the legs. This is triggered by UV radiation, and by hot and cold temperature.
4) Matting type telangiectasia.
5) Reticular varicous veins: in most cases they represent the nourishing veins for the districts that are interested by telangiectasia.

No satisfactory treatment exists for leg telangiectasia and the only possible treatment is aesthetic surgery.

Thus, there is an unsatisfied need of safe and active medical tools to protect a skin that is unusually vulnerable to chemical and physical insults.

Chitosan and its derivatives are amino-polysaccharides, derived from the chitin extracted from the exoskeleton of the crustaceans, known in the art for their use in different preparations. KR20020084672 discloses chitosan as an ingredient of microspheres, useful as a carrier for separation of proteins or peptides; KR20020048534 reports chitosan as an ingredient of a pack composition for skin massage, including paraffin wax as an effective component; JP2005306746 is teaching the use of chitosan to obtain a wrinkle therapeutic agent as an ingredient of gel-like or spongy preparations of botulinum toxin. WO2005055924 reports chitosan derivatives as ingredients of hydrogels useful for cavity-filling wound dressings. JP2004231604 teaches compositions of chitosans having a high deacetylation degree, as an ingredient of a carrier sheet with a porous spongy texture. WO03042251 discloses compositions comprising chitosan in the form of a network of nano-sized fibres. WO02057983 discloses a multi-layered, air gap sheet of chitosan with a regular lamellar structure which retains drugs for a prolonged period of time; JP11060605 teaches an amphiphilic chitosan derivative which can be used as dispersion stabilizer or emulsifier in a drug for application to skin. Finally, EP1303249, discloses a nail varnish composition containing at least one antimycotic agent and an hydroxyalkyl or a carboxyalkyl chitosan, whereas WO2004/112814 discloses a nail restructuring composition based on one herb extract from the genus *Equisetum* in combination with hydroxypropyl chitosan.

BRIEF SUMMARY OF THE INVENTION

The object of the present invention is thus represented by a pharmaceutical and/or cosmetic composition containing:
(A) at least chitosan, a chitosan derivative and/or a physiologically acceptable salt thereof, and;
(B) at least a $C_6$-$C_{12}$-dicarboxylic acid amide and/or a physiologically acceptable salt thereof.

Said composition is useful to form a film after application onto the skin and drying, that protects the skin of the face and the other areas affected by rosacea as well as by other skin conditions characterized by telangiectasia.

Among chitosan derivatives, water soluble chitosans are preferred; hydroxyalkyl chitosans, such as hydroxypropyl chitosan, being the most preferred water soluble chitosans derivatives.

Among the $C_5$-$C_{12}$-dicarboxylic acids, $C_8$-$C_{10}$-dicarboxylic acids are particularly preferred, $C_9$-dicarboxylic acids being the most preferred; according to additional preferred embodiments, such dicarboxylic acids are linear and/or alkyl acids.

The $C_6$-$C_{12}$-dicarboxylic acid amide which is used for the purposes, of the present invention is preferably represented by the following formula:

wherein:
"n" is comprised between 4 and 10, preferably between 6 and 8 and, more preferably, it is 7;
R is a —N(R')(R") group, wherein:
R' is H or a $C_1$-$C_4$-alkyl group, and
R" is H, a $C_1$-$C_4$-alkyl group or a $C_1$-$C_4$-carboxy group.

According to preferred embodiments, said $C_1$-$C_4$-alkyl groups are methyl or ethyl whereas said $C_1$-$C_4$-carboxy group is carboxy methyl.

The preferred $C_6$-$C_{12}$-dicarboxylic acid is azelaic acid.

Among $C_6$-$C_{12}$-dicarboxylic acid amides, azelaic acid amides, such as azeloyl diglycine, are thus preferred, and may be in form of a salt, preferably a sodium or potassium salt, such as potassium azeloyl diglycinate.

The composition according to the present invention may be applied by a gently massage on the skin, or may be sprayed by allowing the formation of an elastic film after drying. The composition according to the present invention allows a long lasting intimate contact and continuous protection of the skin for many hours after the application.

Compositions according to the present invention are in the form are in the form of liquid, semiliquid or semisolid preparations, including solutions, suspensions, lotions, emulsions, colloids, creams, gels, with a content in component A from 0.1 to 10 wt. % (percentages by weight are given with respect to the whole preparation), including from 0.2 to 5 wt. %, and including from 0.25 to 2.0 wt. % and with a content in component B from 0.1 to 30 wt. % (percentages by weight are given with respect to the whole preparation), from 0.25 to 25 wt. %, including from 0.5 to 20 wt. %.

According to one embodiment, component (A) is present in amounts of from 0.5 to 1.5 wt. % (including about 1 wt. %) and component (B) is present in amounts of from 2.5 to 7.5 wt. % (including about 5 wt. %), with respect to the weight of the whole composition.

Compositions according to the present invention are superior to the conventional formulations, in that they leave a uniform and invisible film.

Moreover, compositions according to the present invention do not dirty, do not dry like gels and lotions do, and do not give bothersome sensation when applied, like other rigid film preparations do.

Pharmaceutical compositions are prepared according to conventional technique, using compatible excipients, adjuvants and/or pharmaceutically or cosmetically acceptable carriers, and may contain, in combination, other active principles with complementary or, in any case, useful activity.

Examples of these compositions prepared according to the present invention include: solutions, emulsions, suspensions, colloids, creams, gels, for application to affected skin.

The compositions according to the present invention may contain one or more additional ingredients selected from solvents, sunscreens, skin-conditioning agents, emollients, moisturizers, emulsifying agents, viscosity-increasing agents, UV-A filters, plant extracts, antioxidants.

BRIEF DESCRIPTION OF THE DRAWINGS

FIG. 1. Percentages of subjects by flushing severity at baseline at end of treatment.

DETAILED DESCRIPTION OF THE INVENTION

It has now surprisingly been found that preparations containing chitosan or its derivatives, and at least the amide of a short-medium chain (from 6 to 12 carbon atoms) aliphatic dicarboxylic acid may form an elastic film onto the skin, after application and drying, suitable to protect the skin from chemical or physical insults. The two components of the film, saccharidic and lipidic, act in a synergistic way and have a protective activity superior to that of the two components alone.

The film forming compositions according to the present invention may easily be sprayed onto the skin surface, by allowing quick drying and easy formation of an elastic film, that avoids bothersome sensation of oily skin. The film forming compositions according to the present invention may also be applied on the skin by gently massage. The film formed after drying protects the skin from the insult of both hot and cold temperature, decreases the inflammation due to ultraviolet radiation and prevents the growth of microorganisms by coating them and inhibiting their vital functions.

A composition comprising:
(A) at least chitosan, a hydroxyalkyl chitosan and/or a physiologically acceptable salt thereof, and;
(B) at least a linear and/or alkyl $C_6$-$C_{12}$-dicarboxylic acid amide and/or a physiologically acceptable salt thereof, such a
composition wherein the hydroxyalkyl chitosan is water soluble, such a
composition wherein the hydroxyalkyl chitosan is hydroxypropyl chitosan, such a
composition wherein the physiologically acceptable salt of the chitosan, hydroxyalkyl chitosan and/or $C_6$-$C_{12}$-dicarboxylic acid amide is a sodium and/or potassium salt, such a
composition wherein the $C_6$-$C_{12}$-dicarboxylic acid is a $C_8$-$C_{10}$-dicarboxylic acid, such a
composition wherein the $C_6$-$C_{12}$-dicarboxylic acid is a $C_9$-dicarboxylic acid, such a
composition wherein the dicarboxylic acid is azelaic acid, such a
composition wherein the $C_6$-$C_{12}$-dicarboxylic acid amide has the following formula:

wherein:
i) n is comprised between 4 and 10;
ii) R is a —N(R')(R") group, wherein:
a) R' is H or a $C_1$-$C_4$-alkyl group, and
b) R" is H, a $C_1$-$C_4$-alkyl group or a $C_1$-$C_4$-carboxy group, such a
composition wherein n is comprised between 6 and 8, such a
composition wherein n is 7, such a
composition wherein the $C_1$-$C_4$-alkyl group is methyl and/or ethyl and the $C_1$-$C_4$-carboxy group is carboxy methyl, such a
composition, wherein the $C_6$-$C_{12}$-dicarboxylic acid amide is azeloyl diglycine, such a
composition wherein the $C_6$-$C_{12}$-dicarboxylic acid amide salt is potassium azeloyl diglycinate, such a
composition wherein component (A) is present in an amount from 0.1 to 10 wt. % of the composition, such a composition wherein component (A) is present in an amount from 0.2 to 5 wt. % of the composition, such a composition wherein component (A) is present in an amount from 0.25 to 2.0 wt. % of the composition, such a composition wherein component (B) is present in an amount from 0.1 to 30 wt. % of the composition, such a composition wherein component (B) is present in an amount from 0.25 to 25 wt. % of the composition, such a composition wherein component (B) is present in an amount from 0.5 to 20 wt. % of the composition, such a composition wherein component (A) is present in an amount from 0.5 to 1.5 wt. % and component (B) is present in an amount from 2.5 to 7.5 wt. % of the composition, such a composition wherein component (A) is present in an amount of about 1 wt. % and component (B) is present in an amount of about 5 wt. % of the composition, such a composition in liquid, semiliquid or semisolid form, selected from a solution, suspension, lotion, emulsion, colloid, cream and gel, such a composition further comprising pharmaceutically and/or cosmetically acceptable active ingredients, excipients, adjuvants and/or carriers, such a method for the treatment and/or prevention of rosacea, comprising administering to a living human or animal subject in need thereof, the composition, such a method for the treatment and/or prevention of telangiectasia, comprising administering to a living human or animal subject in need thereof, the composition, such a method wherein the telangiectasia is leg telangiectasia, such a method for the treatment and/or prevention of couperose, comprising administering to a living human or animal subject in need thereof, the composition.

The pharmaceutical compositions and the uses of the present invention will now be more fully described by the following examples. It should, however, be noted that such examples are given by way of illustration and not of limitation.

EXAMPLE 1

An oil in water cream having the following w/w % composition was prepared:

| 1. POTASSIUM PALMITOYL HYDROLYZED WHEAT PROTEIN | 1.00% |
|---|---|
| 2. GLYCERYL STEARATE | 2.00% |
| 3. CETEARYL ALCOHOL | 2.00% |
| 4. GLYCERYL STEARATE SE | 1.00% |
| 5. DICAPRYLYL ETHER | 4.00% |
| 6. ETHYLHEXYL METHOXYCINNAMATE | 4.00% |
| 7. BUTYL METHOXYDIBENZOYLMETHANE | 1.00% |
| 8. LECITHIN | 0.02% |
| 9. TOCOPHEROL | 0.001% |
| 10. ASCORBYL PALMITATE | 0.001% |
| 11. CITRIC ACID | 0.001% |
| 12. TOCOPHERYL ACETATE | 0.50% |
| 13. PURIFIED WATER | 81.00% |
| 14. HYDROXYPROPYL CHITOSAN | 0.50% |
| 15. XANTHAN GUM | 0.50% |
| 16. DENATURATED ETHYL ALCOHOL | 1.00% |
| 17. PHENETHYL ALCOHOL | 0.50% |
| 18. CAPRYLYL GLYCOL | 0.50% |
| 19. POTASSIUM AZELOYL DIGLYCINATE | 0.50% |

Preparation

Phase A: Hydroxypropyl chitosan was dispersed in ca. 50% by weight of total water until a clear solution was obtained. The solution was heated at 65° C.±2° C. and Xanthan gum was added and stirred until a homogenous solution was obtained.

Phase B: Potassium palmitoyl, Glyceryl Stearate, Cetearyl Alcohol, Glyceryl Stearate SE, Dicaprylyl Ether, Ethylehexyl methoxycinnamate, Butyl methoxydibenzoyl-methane, Lecithin, Tocopherol, Ascorbyl Palmitate, Citric Acid and Tocopheryl Acetate were mixed together and heated at 65° C.±2° C.

Phase B was added to Phase A under agitation (turbo) to allow the emulsification. The resulting emulsion was cooled to 35° C.±2° C. under continuous mixing.

Caprylyl Glycol dissolved into Phenethyl Alcohol, Potassium Azeloyl Diglycinate dissolved in the rest of purified water (50% wt) and Ethyl Alcohol were mixed into the emulsion at the end of preparation. The product was kept under gentle agitation until a homogenous oil in water cream was obtained.

EXAMPLE 2

An oil in water cream having the following w/w % composition was prepared:

| 1. POTASSIUM PALMITOYL HYDROLYZED WHEAT PROTEIN | 3.00% |
|---|---|
| 2. GLYCERYL STEARATE | 5.00% |
| 3. CETEARYL ALCOHOL | 5.00% |
| 4. GLYCERYL STEARATE SE | 3.00% |
| 5. DICAPRYLYL ETHER | 6.00% |
| 6. ETHYLHEXYL METHOXYCINNAMATE | 6.00% |
| 7. BUTYL METHOXYDIBENZOYLMETHANE | 3.00% |
| 8. LECITHIN | 0.04% |
| 9. TOCOPHEROL | 0.01% |
| 10. ASCORBYL PALMITATE | 0.01% |
| 11. CITRIC ACID | 0.01% |
| 12. TOCOPHERYL ACETATE | 1.00% |
| 13. PURIFIED WATER | 59.93% |
| 14. HYDROXYPROPYL CHITOSAN | 1.00% |
| 15. XANTHAN GUM | 1.00% |
| 16. DENATURATED ETHYL ALCOHOL | 3.00% |
| 17. PHENETHYL ALCOHOL | 1.00% |
| 18. CAPRYLYL GLYCOL | 1.00% |
| 19. POTASSIUM AZELOYL DIGLYCINATE | 1.00% |

Preparation

The formulation was prepared by using the same method described for Example 1.

EXAMPLE 3

An oil in water cream having the following w/w % composition was prepared:

| 1. POTASSIUM PALMITOYL HYDROLYZED WHEAT PROTEIN | 2.00% |
|---|---|
| 2. CETEARYL ALCOHOL | 5.00% |
| 3. GLYCERYL STEARATE SE | 3.00% |
| 4. DICAPRYLYL ETHER | 5.00% |
| 5. ETHYLHEXYL METHOXYCINNAMATE | 4.00% |
| 6. LECITHIN | 0.04% |
| 7. ASCORBYL PALMITATE | 0.01% |
| 8. CITRIC ACID | 0.01% |
| 9. TOCOPHERYL ACETATE | 1.00% |
| 10. PURIFIED WATER | 72.94% |
| 11. HYDROXYPROPYL CHITOSAN | 1.00% |
| 12. XANTHAN GUM | 1.00% |
| 13. DENATURATED ETHYL ALCOHOL | 3.00% |
| 14. PHENETHYL ALCOHOL | 1.00% |
| 15. POTASSIUM AZELOYL DIGLYCINATE | 1.00% |

Preparation

Phase A: Hydroxypropyl chitosan was dispersed in ca. 50% by weight of total water until a clear solution was obtained. The solution was heated at 65° C.±2° C. and Xanthan gum was added and stirred until a homogenous solution was obtained.

Phase B: Potassium palmitoyl, Cetearyl Alcohol, Glyceryl Stearate SE, Dicaprylyl Ether, Ethylehexyl methoxycinnamate, Lecithin, Ascorbyl Palmitate, Citric Acid and Tocopheryl Acetate were mixed together and heated at 65° C.±2° C.

Phase B was added to Phase A under agitation (turbo) to allow the emulsification. The resulting emulsion was cooled to 35° C.±2° C. under continuous mixing.

Phenethyl Alcohol, Potassium Azeloyl Diglycinate dissolved in the rest of purified water (50% wt) and Ethyl Alcohol were mixed into the emulsion at the end of preparation. The product was kept under gentle agitation until a homogenous oil in water cream was obtained.

EXAMPLE 4

An oil in water cream having the following w/w % composition was prepared:

| | | |
|---|---|---|
| 1. | POTASSIUM PALMITOYL HYDROLYZED WHEAT PROTEIN | 2.00% |
| 2. | GLYCERYL STEARATE | 4.00% |
| 3. | CETEARYL ALCOHOL | 4.00% |
| 4. | GLYCERYL STEARATE SE | 2.00% |
| 5. | DICAPRYLYL ETHER | 5.00% |
| 6. | ETHYLHEXYL METHOXYCINNAMATE | 8.00% |
| 7. | BUTYL METHOXYDIBENZOYLMETHANE | 2.00% |
| 8. | BIS-ETHYLHEXYLOXYPHENOL METHOXYPHENYL TRIAZINE | 3.00% |
| 9. | LECITHIN | 0.040% |
| 10. | TOCOPHEROL | 0.002% |
| 11. | ASCORBYL PALMITATE | 0.002% |
| 12. | CITRIC ACID | 0.002% |
| 13. | TOCOPHERYL ACETATE | 0.20% |
| 14. | HYDROXYPROPYL CHITOSAN | 1.00% |
| 15. | XANTHAN GUM | 0.30% |
| 16. | DENATURED ETHYL ALCOHOL | 2.00% |
| 17. | PHENETHYL ALCOHOL | 0.50% |
| 18. | CAPRYLYL GLYCOL | 0.50% |
| 19. | POTASSIUM AZELOYL DIGLYCINATE | 0.50% |
| 20. | PURIFIED WATER | q.s to 100.00% |

Preparation

The preparation was made as in Example 1. A homogenous oil in water cream was obtained.

EXAMPLE 5

A comparative evaluation of the inhibition of VEGF (Vascular Endothelial Growth Factor) release on human 3D artificial skin was tested by the preparation as per the Example 4, compared to two different preparations, respectively named LPOL2899A (same as per the Example 4, but not containing POTASSIUM AZELOYL DIGLYCINATE), LPOL2899B (same as per the Example 4, but not containing HYDROXYPROPYL CHITOSAN) and LPOL2899C (same as per the Example 4, but not containing either POTASSIUM AZELOYL DIGLYCINATE or HYDROXYPROPYL CHITOSAN).

The effect of the four preparations was tested on the inhibition of Vascular Endothelial Growth Factor (VEGF) production induced by a pro-inflammatory stimulus on 3D human epidermis. VEGF is a strong angiogenic protein that significantly influences the vessels permeability and is constitutively expressed in keratinocytes, i.e. the cells of the skin. Under stressful conditions, such as exposure to soluble inflammation mediator like IL-1α, epidermal keratinocytes increase the synthesis and release of VEGF.

Epidermis units have been treated with IL-1α in the cell medium to induce an increase in the VEGF synthesis, and at the same time treated applying the investigated samples undiluted on the epidermis corneous layer. Following 24 h treatment, the cell culture medium below the epidermis units was collected and analyzed for the VEGF content through an ELISA assay.

The tested samples were the preparation as per the Example 4 and the two comparative preparations LPOL2899A and LPOL2899B. Skin units treated with IL-1α only have been used as positive controls. The experiment was carried out in three replicas.

In vitro test system employed consists of a tridimensional artificial system of human epidermis (Mattek, USA) i.e. a reconstructed artificial human skin model comprising normal human epidermal keratinocytes, growing as an integrated three-dimensional cell culture model, perfectly mimicking the human skin in vitro. The model exhibits normal barrier functions (presence of a differentiated stratum corneum).

About 20 mg of each undiluted sample was applied on an epidermis unit in three replicas, the exposure was 30' following the product application, epidermis units, except the controls, were treated for 2 h with 500 pg/ml of IL-1α (Prospec) in the cell medium to improve VEGF synthesis.

After 2 h the cell medium was removed and changed. The incubation of the samples was carried out up to 24 hours at 37° C., 5% $CO_2$.

As positive control epidermis units treated with IL-1α only were used. At the end of the exposure period, the products were removed, the tissue gently washed with phosphate buffer (PBS) for further MIT and viability assay, and the culture medium was collected for the VEGF assay.

The VEGF release assay following IL-1α treatment, 500 pg/ml, with and without treatment with the samples is reported in the following table.

| Sample | VEGF pg/ml (DS %) | % inhibition |
|---|---|---|
| Preparation of Example 4 + 500 pg/ml IL-1α | 313.21 (26.9) | 46.4 |
| LPOL 2899A + 500 pg/ml IL-1α | 386.03 (4.6) | 33.9 |
| LPOL 2899B + 500 pg/ml IL-1α | 433.86 (6.9) | 25.7 |
| LPOL 2899C + IL-1α | 477.25 (4.1) | 18.3 |
| 500 pg/ml IL-1α (positive control) | 583.93 (7.5) | --- |

The preparation containing the vehicle, but not the two ingredients potassium azeloyl diglycinate and hydroxypropyl chitosan, inhibited the IL-1α induced VEGF release by only 18%. The effect of the preparation containing hydroxypropyl chitosan was 25.7% inhibition and that of the preparation containing potassium azeloyl diglycinate was 33.9% inhibition. The preparation as per Example 4 had the strongest inhibitory effect (46.4% inhibition) confirming a synergistic activity of the two components on the protection of skin against the insult of IL-1α.

EXAMPLE 6

An oil in water cream having the following w/w % composition was prepared:

| | |
|---|---|
| 1. POTASSIUM PALMITOYL HYDROLYZED WHEAT PROTEIN | 0.80% |
| 2. GLYCERYL STEARATE | 1.60% |
| 3. CETEARYL ALCOHOL | 1.60% |
| 4. GLYCERYL STEARATE SE | 2.00% |
| 5. DICAPRYLYL ETHER | 5.00% |
| 6. ETHYLHEXYL METHOXYCINNAMATE | 8.00% |
| 7. BUTYL METHOXYDIBENZOYLMETHANE | 2.00% |
| 8. BIS-ETHYLHEXYLOXYPHENOL METHOXYPHENYL TRIAZINE | 3.00% |
| 9. LECITHIN | 0.037% |
| 10. TOCOPHEROL | 0.006% |
| 11. ASCORBYL PALMITATE | 0.005% |
| 12. CITRIC ACID | 0.002% |
| 13. TOCOPHERYL ACETATE | 0.20% |
| 14. CHITOSAN | 1.00% |
| 15. XANTHAN GUM | 0.02% |
| 16. DENATURATED ETHYL ALCOHOL | 2.00% |
| 17. PHENETHYL ALCOHOL | 0.50% |
| 18. CAPRYLYL GLYCOL | 0.50% |
| 19. POTASSIUM AZELOYL DIGLYCINATE | 5.00% |
| 20. LACTIC ACID | 0.50% |
| 21. PURIFIED WATER | q.s to 100.00% |

Preparation

The preparation was made according to Example 1 of International patent application PCT/EP2009/059749, with lactic acid added to help dissolve chitosan. A homogeneous oil in water cream was obtained.

EXAMPLE 7

An evaluation of the soothing activity on rosacea was tested by the preparation as per Example 6.

The study was performed in 4 female volunteers with light/moderate rosacea. The tested product was applied to the face of the women by a trained technician, by gloved fingers and light massage, and left to be absorbed on the skin for at least 15 minutes.

Soothing Effect on Skin Redness

The soothing efficacy of the product under study on skin redness was evaluated trough spectrophotometrical measurement of the skin color at level of the face, immediately before (T0), 20 minutes and 4 hours after application of the composition.

Spectrophotometrical evaluations were performed by a visible-UV-IR spectrophotometer (λ from 300 to 900 nm) which use a tungsten halogen lamp and a deuterium lamp in accordance with CIE (Commission Internationale de l'Eclarage). The lamps were switched on 30 minutes before instrument use in order to provide a stable emission.

The measurement angle was 90° (position of the probe on the skin) and the measured area was 2 mm². The wavelength range was 380-780 nm corresponding to the visible light spectrum.

Contact Thermographs of Skin

Contact thermography permits visualising, through colors, the temperatures of the areas being examined by using encapsulated liquid crystals plates. Each color of the liquid crystal corresponds to a different temperature following a standard chromatic scale: higher temperatures are shown by the colors blue and violet, while lower temperatures by green, brown and black. According to a photographic scale the investigator judged skin temperature variations:

0=uniform hyperthermal image
1=shaded spots thermal image (hyperthermal images)
2=leopard spots (numerous hyperthermal images)
3=hypothermal black holes
4=uniform hypothermal image Contact thermographs were performed at level of the face at T0, and 20 minutes and 4 hours from product application.

Results

The composition as per Example 6 determined a reduction of skin redness, measured as an increase of spectrum total area compared to baseline yet 20 minutes after application. The reduction over baseline value was in mean 8.6% after 20 minutes and 10.6% after 4 hours.

Concerning the evaluation performed by contact thermography on the face, both after 20 minutes and 4 hours from the application of the composition according to the Example 6 the visual score improved by 44.4% versus baseline conditions.

It is concluded that the composition according to Example 6 is effective in decreasing redness and skin temperature in subjects with rosacea.

EXAMPLE 8

An oil in water cream having the following w/w % composition was prepared:

| | |
|---|---|
| 1. POTASSIUM PALMITOYL HYDROLYZED WHEAT PROTEIN | 2.00% |
| 2. GLYCERYL STEARATE | 4.00% |
| 3. CETEARYL ALCOHOL | 4.00% |
| 4. GLYCERYL STEARATE SE | 2.00% |
| 5. DICAPRYLYL ETHER | 5.00% |
| 6. ETHYLHEXYL METHOXYCINNAMATE | 8.00% |
| 7. BUTYL METHOXYDIBENZOYLMETHANE | 2.00% |
| 8. BIS-ETHYLHEXYLOXYPHENOL METHOXYPHENYL TRIAZINE | 3.00% |
| 9. LECITHIN | 0.035% |
| 10. TOCOPHEROL | 0.0075% |
| 11. ASCORBYL PALMITATE | 0.005% |
| 12. CITRIC ACID | 0.0025% |
| 13. TOCOPHERYL ACETATE | 0.20% |
| 14. HYDROXYPROPYL CHITOSAN | 1.00% |
| 15. XANTHAN GUM | 0.30% |
| 16. DENATURATED ETHYL ALCOHOL | 2.00% |
| 17. PHENETHYL ALCOHOL | 0.50% |
| 18. CAPRYLYL GLYCOL | 0.50% |
| 19. POTASSIUM AZELOYL DIGLYCINATE | 5.00% |
| 20. PURIFIED WATER | q.s to 100.00% |

Preparation

The preparation was made as in Example 1. A homogenous oil in water cream was obtained.

EXAMPLE 9

An evaluation of the activity on microcirculation was tested by the preparation as per the Example 8 and compared with the commercial product FINACEA® gel, containing 15% azelaic acid as active ingredient and approved for the treatment of rosacea.

The study was performed in 4 healthy female volunteers. The two products were applied to the face of the women, one product to the left side, and one product to the right side, randomly, by a trained technician, by gloved fingers and light massage, and left to be absorbed on the skin for at least 15 minutes.

Laser Doppler flowmetry was performed by means of Periflux laser Doppler flowmeter (Perimed, Italy) at baseline (T0, before product application, 20 minutes (T20 min) and 3 hours (T3h) after product application. Laser Doppler flowmetry is a well-established technique for the real-time measurement of dermal blood flow.

The results were as follows:

The preparation as per Example 8 demonstrated a significant reduction of the microcirculation flow (−43%) at 20 minutes after the application, and the capillary vessels were less visible than at T0, indicating a soothing activity of the preparation. The effect was still evident after 3 hours (−13%). Conversely, the commercial product FINACEA® gel caused an immediate increase of the microcirculation flow (+187%) associated to a mild pinching sensation, a sign of irritating and flushing activity. The data are summarized in Table 1.

Results: The erythema score, assessed by means of mexameter, has shown a decrease from baseline to any post-baseline time point (including end of follow-up visit) in all evaluated areas and in the composite index, compared to small or no changes observed in the placebo group. In the between groups comparison at the end of treatment, a statistically significant superiority of the preparation as per Example 8 over placebo was reported in all examined areas and in the composite score. The data are provided in Table 2.

TABLE 2

Difference of erythema score measured at day 28 versus baseline in different face areas and composite score, after application of P-3075 (preparation as per Example 8) or placebo. The between groups differences were all statistically significant (alpha = 0.05)

|  | FRONT | RIGHT CHEEK | LEFT CHEEK | CHIN | COMPOSITE SCORE |
|---|---|---|---|---|---|
| Δ P-3075 VS BASELINE (day 28) | −52.4 | −66.3 | −55.0 | −63.7 | −237.3 |
| Δ PLACEBO VS BASELINE (day 28) | −11.3 | −21.7 | −12.7 | −3.5 | −46.8 |
| GROUPS DIFFERENCE P-VALUE | 0.0041 | 0.0025 | 0.0019 | 0.0011 | 0.0000 |

TABLE 1 differences of microcirculation blood flow al 20 min and 3 hours after application of preparation as per Example 8 or FINACEA ® gel.

| Product | T20 min versus T0 | T3 h versus T0 |
|---|---|---|
| Preparation as per Example 8 | −43% | −13% |
| FINACEA ® 15% gel | +187% | −3% |

Discussion: Rosacea is a skin condition characterized by erythema, flushing, redness and dilation of superficial blood vessels (telangiectasia) of various areas of the face. Commercially available treatments are inconclusive and FINACEA® gel (15% azelaic acid), one of the most recently approved treatments for rosacea, increased the microcirculation blood flow in this investigation, instead of decreasing it. On the contrary, the composition according to the Example 8 was surprisingly effective in decreasing the capillary blood flow as measured by laser Doppler flowmetry, thus providing a therapeutic effect in subjects with rosacea.

EXAMPLE 10

An evaluation of the activity on skin hydration and on erythema of patients with rosacea was tested by the preparation as per Example 8 (code P-3075) and compared with an inactive placebo, i.e. a matching cream containing the same vehicle, but devoid of the active ingredients hydroxypropyl chitosan and azeloyl diglycinate.

A total number of 42 patients were randomized: 28 were treated with the preparation as per Example 8 and 14 with placebo. Each subject applied the assigned treatment, twice a day for 4 weeks. The treatment phase was followed by a follow-up period of other 2 weeks. The evaluation of erythema (skin redness) was performed at day 7, 14, 28 (end of treatment) and 42 (end of follow up) in 4 different areas of the face: front, right and left cheek and chin. In addition, the composite score obtained as the sum of the 4 scores for each patient was calculated and analyzed. Erythema was assessed both instrumentally, by means of mexameter, and clinically.

In the clinical assessment of erythema, an improvement from baseline was observed in the preparation as per Example 8 (P-3075) group throughout the study, compared to no substantial changes in the placebo group. The results at Day 28 (end of treatment) showed that, in the P-3075 group, flushing was absent in 3 patients (10.7%), mild in 17 (60.7), moderate in 7 (25.0%) and severe in 1 (3.6%), while, in the placebo group, flushing was mild in 5 (35.7%) and moderate in 9 (64.3%). The data are shown in FIG. 1.

In conclusion, the preparation according to the present invention administered for 28 days in patients with rosacea was effective in skin protection by reducing erythema, evaluated both instrumentally and clinically. Superiority over placebo was reported in all examined areas and in the composite score.

The invention claimed is:

1. A composition comprising:
   (A) hydroxypropyl chitosan or a physiologically acceptable salt thereof, and;
   (B) a linear and/or alkyl $C_6$-$C_{12}$-dicarboxylic acid amide of the following formula:

ROC—$(CH_2)_n$—COR wherein:
   i) n is comprised between 4 and 10;
   ii) R is a —N(R')(R") group, wherein:
      a) R' is H or a $C_1$-$C_4$-alkyl group, and
      b) R" is H, a $C_1$-$C_4$-alkyl group or a $C_1$-$C_4$-carboxy group,
   and/or a physiologically acceptable salt thereof,
   wherein component (A) is present in an amount from 0.25 to 2.0 wt. % of the composition and component (B) is present in an amount from 0.5 to 20 wt. % of the composition.

2. The composition of claim 1, wherein the physiologically acceptable salt of the hydroxypropyl chitosan and/or $C_6$-$C_{12}$-dicarboxylic acid amide is a sodium and/or potassium salt.

3. The composition of claim 1, wherein the $C_6$-$C_{12}$-dicarboxylic acid amide is a $C_8$-$C_{10}$-dicarboxylic acid amide.

4. The composition of claim 3, wherein the $C_6$-$C_{12}$-dicarboxylic acid amide is a $C_9$-dicarboxylic acid amide.

5. The composition of claim 1, wherein the dicarboxylic acid amide is azelaic acid amide.

6. The composition of claim 1, wherein n is comprised between 6 and 8.

7. The composition of claim 6, wherein n is 7.

8. The composition of claim 1, wherein the $C_1$-$C_4$-alkyl group is methyl and/or ethyl and the $C_1$-$C_4$-carboxy group is carboxy methyl.

9. The composition of claim 1, wherein the $C_6$-$C_{12}$-dicarboxylic acid amide is azeloyl diglycine.

10. The composition of claim 1, wherein the $C_6$-$C_{12}$-dicarboxylic acid amide salt is potassium azeloyl diglycinate.

11. The composition of claim 1, wherein component (A) is present in an amount from 0.5 to 1.5 wt. % and component (B) is present in an amount from 2.5 to 7.5 wt. % of the composition.

12. The composition of claim 1, wherein component (A) is present in an amount of about 1 wt. % and component (B) is present in an amount of about 5 wt. % of the composition.

13. The composition of claim 1, in liquid, semiliquid or semisolid form, selected from a solution, suspension, lotion, emulsion, colloid, cream and gel.

14. The composition of claim 1, further comprising pharmaceutically and/or cosmetically acceptable active ingredients, excipients, adjuvants and/or carriers.

15. A method for the treatment of rosacea, comprising administering to a living human or animal subject in need thereof, the composition of claim 1.

\* \* \* \* \*